(12) United States Patent
Kaduchak et al.

(10) Patent No.: US 8,863,958 B2
(45) Date of Patent: *Oct. 21, 2014

(54) APPARATUS FOR SEPARATING PARTICLES UTILIZING ENGINEERED ACOUSTIC CONTRAST CAPTURE PARTICLES

(75) Inventors: Gregory Kaduchak, Los Alamos, NM (US); Michael D. Ward, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/295,934

(22) Filed: Nov. 14, 2011

(65) Prior Publication Data

US 2012/0055853 A1    Mar. 8, 2012

Related U.S. Application Data (63) Continuation of application No. 11/784,928, filed on Apr. 9, 2007, now Pat. No. 8,083,068.

(51) Int. Cl.
  *B03D 3/06* (2006.01)
  *B01D 21/28* (2006.01)
(52) U.S. Cl.
  CPC .................................. *B01D 21/283* (2013.01)
  USPC .................................................. 209/5; 209/4
(58) Field of Classification Search
  USPC ................................ 209/158, 590, 638, 4, 5
  See application file for complete search history.

(56) References Cited

U.S. PATENT DOCUMENTS

| | | |
|---|---|---|
| 2,900,536 A | 8/1959 | Palo |
| 3,882,732 A | 5/1975 | Fletcher et al. |
| 4,055,491 A | 10/1977 | Porath-Furedi |
| 4,265,124 A | 5/1981 | Lim et al. |
| 4,285,810 A | 8/1981 | Kirkland et al. |
| 4,350,683 A | 9/1982 | Galfre et al. |
| 4,434,230 A | 2/1984 | Ritts, Jr. |

(Continued)

FOREIGN PATENT DOCUMENTS

| | | |
|---|---|---|
| CN | 1493831 A | 5/2004 |
| CN | 1524948 | 9/2004 |

(Continued)

OTHER PUBLICATIONS

Aboobaker, N. et al., "Mathematical modeling of the movement of suspended particles subjected to acoustic and flow fields", *App. Math. Modeling*, 2005, 29, 515-532.

(Continued)

*Primary Examiner* — Joseph C Rodriguez
*Assistant Examiner* — Kalyanavenkateshware Kumar
(74) *Attorney, Agent, or Firm* — Baker & Hostetler LLP (57) ABSTRACT

An apparatus for separating particles from a medium includes a capillary defining a flow path therein that is in fluid communication with a medium source. The medium source includes engineered acoustic contrast capture particle having a predetermined acoustic contrast. The apparatus includes a vibration generator that is operable to produce at least one acoustic field within the flow path. The acoustic field produces a force potential minima for positive acoustic contrast particles and a force potential minima for negative acoustic contrast particles in the flow path and drives the engineered acoustic contrast capture particles to either the force potential minima for positive acoustic contrast particles or the force potential minima for negative acoustic contrast particles.

20 Claims, 3 Drawing Sheets

(56) References Cited

U.S. PATENT DOCUMENTS

| | | | |
|---|---|---|---|
| 4,492,752 A | 1/1985 | Hoffman et al. | |
| 4,523,682 A | 6/1985 | Barmatz et al. | |
| 4,523,982 A | 6/1985 | Lee | |
| 4,596,464 A | 6/1986 | Hoffman et al. | |
| 4,604,542 A | 8/1986 | Thompson | |
| 4,673,512 A | 6/1987 | Schram | |
| 4,743,361 A | 5/1988 | Schram | |
| 4,759,775 A * | 7/1988 | Peterson et al. | 210/708 |
| 4,777,823 A | 10/1988 | Barmatz et al. | |
| 4,790,653 A | 12/1988 | North, Jr. | |
| 4,845,025 A | 7/1989 | Lary et al. | |
| 4,867,559 A | 9/1989 | Bach | |
| 4,877,516 A | 10/1989 | Schram | |
| 4,913,883 A | 4/1990 | Imai et al. | |
| 4,964,303 A | 10/1990 | Barmatz et al. | |
| 4,979,824 A | 12/1990 | Mathies et al. | |
| 4,987,086 A | 1/1991 | Brosnan et al. | |
| 4,991,923 A | 2/1991 | Kino et al. | |
| 5,006,266 A | 4/1991 | Schram | |
| 5,030,002 A | 7/1991 | North, Jr. | |
| 5,032,381 A | 7/1991 | Bronstein et al. | |
| 5,040,890 A | 8/1991 | North, Jr. | |
| 5,079,959 A | 1/1992 | Miyake et al. | |
| 5,085,783 A | 2/1992 | Feke et al. | |
| 5,106,187 A | 4/1992 | Bezanson | |
| 5,164,094 A | 11/1992 | Stuckart | |
| 5,225,089 A | 7/1993 | Benes et al. | |
| 5,264,906 A | 11/1993 | Ferer et al. | |
| 5,346,670 A | 9/1994 | Renzoni et al. | |
| 5,376,551 A | 12/1994 | Yoshikami | |
| 5,395,588 A | 3/1995 | North, Jr. et al. | |
| 5,430,541 A | 7/1995 | Sapp | |
| 5,491,344 A | 2/1996 | Kenny et al. | |
| 5,504,337 A | 4/1996 | Lakowicz et al. | |
| 5,527,460 A | 6/1996 | Trampler et al. | |
| 5,528,045 A | 6/1996 | Hoffman et al. | |
| 5,547,849 A | 8/1996 | Baer et al. | |
| 5,626,767 A | 5/1997 | Trampler et al. | |
| 5,644,388 A | 7/1997 | Maekawa et al. | |
| 5,674,698 A | 10/1997 | Zarling et al. | |
| 5,688,406 A | 11/1997 | Dickinson et al. | |
| 5,690,895 A | 11/1997 | Matsumoto et al. | |
| 5,711,888 A | 1/1998 | Trampler et al. | |
| 5,739,902 A | 4/1998 | Gjelsnes et al. | |
| 5,798,222 A | 8/1998 | Goix | |
| 5,800,861 A | 9/1998 | Chiang et al. | |
| 5,831,166 A | 11/1998 | Kozuka et al. | |
| 5,915,925 A | 6/1999 | North | |
| 5,981,180 A | 11/1999 | Chandler et al. | |
| 6,003,388 A | 12/1999 | Oeftering | |
| 6,055,859 A | 5/2000 | Kozuka et al. | |
| 6,074,879 A | 6/2000 | Zelmanovic et al. | |
| 6,090,295 A | 7/2000 | Raghavarae et al. | |
| 6,197,593 B1 | 3/2001 | Deka et al. | |
| 6,216,538 B1 | 4/2001 | Yasuda et al. | |
| 6,221,258 B1 | 4/2001 | Feke et al. | |
| 6,228,652 B1 | 5/2001 | Rodriguez et al. | |
| 6,248,590 B1 | 6/2001 | Malachowski | |
| 6,255,118 B1 | 7/2001 | Alfano et al. | |
| 6,309,886 B1 | 10/2001 | Ambrose et al. | |
| 6,332,541 B1 | 12/2001 | Coakley et al. | |
| 6,348,687 B1 | 2/2002 | Brockmann et al. | |
| 6,373,567 B1 | 4/2002 | Wise et al. | |
| 6,449,563 B1 | 9/2002 | Dukhin et al. | |
| 6,467,350 B1 | 10/2002 | Kaduchak et al. | |
| 6,532,061 B2 | 3/2003 | Ortyn et al. | |
| 6,549,275 B1 | 4/2003 | Cabuz et al. | |
| 6,565,727 B1 | 5/2003 | Shenderov et al. | |
| 6,592,821 B1 | 7/2003 | Wada et al. | |
| 6,604,435 B2 | 8/2003 | Buchanan et al. | |
| 6,644,118 B2 | 11/2003 | Kaduchak et al. | |
| 6,647,739 B1 | 11/2003 | Kim | |
| 6,668,664 B1 | 12/2003 | Ohkawa | |
| 6,683,314 B2 | 1/2004 | Oostman, Jr. et al. | |
| 6,713,019 B2 | 3/2004 | Ozasa et al. | |
| 6,736,904 B2 | 5/2004 | Poniatowski et al. | |
| 6,773,556 B1 | 8/2004 | Brockie et al. | |
| 6,794,671 B2 | 9/2004 | Nicoli et al. | |
| 6,797,158 B2 * | 9/2004 | Feke et al. | 210/97 |
| 6,813,017 B1 | 11/2004 | Hoffman et al. | |
| 6,816,257 B2 | 11/2004 | Goix | |
| 6,831,279 B2 | 12/2004 | Ho | |
| 6,881,314 B1 | 4/2005 | Wang et al. | |
| 6,911,082 B2 | 6/2005 | Sato et al. | |
| 6,929,750 B2 | 8/2005 | Laurell et al. | |
| 6,949,355 B2 | 9/2005 | Yamanishi et al. | |
| 6,982,165 B2 | 1/2006 | Yamakawa et al. | |
| 7,008,540 B1 | 3/2006 | Weavers et al. | |
| 7,018,819 B2 | 3/2006 | Orwar et al. | |
| 7,025,864 B2 | 5/2006 | Durkop et al. | |
| 7,047,809 B2 | 5/2006 | Cobb | |
| 7,052,864 B2 | 5/2006 | Durkop et al. | |
| 7,064,823 B2 | 6/2006 | Roche et al. | |
| 7,081,192 B1 | 7/2006 | Wang et al. | |
| 7,091,348 B2 | 8/2006 | O'Neill et al. | |
| 7,108,137 B2 | 9/2006 | Lal et al. | |
| 7,113,266 B2 | 9/2006 | Wells | |
| 7,161,665 B2 | 1/2007 | Johnson | |
| 7,166,443 B2 | 1/2007 | Walker et al. | |
| 7,190,832 B2 | 3/2007 | Frost et al. | |
| 7,255,780 B2 | 8/2007 | Shenderov | |
| 7,262,838 B2 | 8/2007 | Fritz | |
| 7,267,798 B2 | 9/2007 | Chandler | |
| 7,315,357 B2 | 1/2008 | Ortyn et al. | |
| 7,329,545 B2 | 2/2008 | Pamula et al. | |
| 7,340,957 B2 * | 3/2008 | Kaduchak et al. | 73/570.5 |
| 7,362,432 B2 | 4/2008 | Roth | |
| 7,373,805 B2 | 5/2008 | Hawkes et al. | |
| 7,403,125 B2 | 7/2008 | Rich | |
| 7,431,892 B2 | 10/2008 | Zumeris et al. | |
| 7,477,363 B2 | 1/2009 | Nagai | |
| 7,570,676 B2 | 8/2009 | Essaian et al. | |
| 7,758,811 B2 | 7/2010 | Durack et al. | |
| 7,835,000 B2 | 11/2010 | Graves et al. | |
| 7,837,040 B2 | 11/2010 | Ward et al. | |
| 7,990,525 B2 | 8/2011 | Kanda | |
| 2002/0121285 A1 * | 9/2002 | Poniatowski et al. | 134/1 |
| 2003/0059850 A1 | 3/2003 | Evans | |
| 2004/0057866 A1 * | 3/2004 | Zumeris et al. | 422/20 |
| 2004/0065599 A1 | 4/2004 | Lal et al. | |
| 2005/0072677 A1 | 4/2005 | Gascoyne et al. | |
| 2005/0097968 A1 | 5/2005 | Ishikawa et al. | |
| 2006/0006769 A1 | 1/2006 | Masters et al. | |
| 2006/0021437 A1 * | 2/2006 | Kaduchak et al. | 73/570.5 |
| 2006/0034733 A1 | 2/2006 | Ferren et al. | |
| 2006/0071580 A1 | 4/2006 | Sawada | |
| 2006/0163166 A1 | 7/2006 | Hawkes et al. | |
| 2007/0037172 A1 | 2/2007 | Chiu et al. | |
| 2007/0071683 A1 * | 3/2007 | Dayton et al. | 424/9.5 |
| 2007/0098232 A1 | 5/2007 | Matula et al. | |
| 2007/0119239 A1 | 5/2007 | Priev et al. | |
| 2008/0053787 A1 | 3/2008 | Bagajewicz | |
| 2008/0245709 A1 | 10/2008 | Kaduchak et al. | |
| 2008/0245745 A1 * | 10/2008 | Ward et al. | 210/748 |
| 2009/0029870 A1 | 1/2009 | Ward et al. | |
| 2009/0038932 A1 | 2/2009 | Denslow et al. | |
| 2009/0042239 A1 | 2/2009 | Ward et al. | |
| 2009/0042310 A1 | 2/2009 | Ward et al. | |
| 2009/0045107 A1 | 2/2009 | Ward et al. | |
| 2009/0048805 A1 | 2/2009 | Kaduchak et al. | |
| 2009/0050573 A1 | 2/2009 | Ward et al. | |
| 2009/0053686 A1 * | 2/2009 | Ward et al. | 435/2 |
| 2009/0107241 A1 | 4/2009 | Goddard et al. | |
| 2009/0139332 A1 | 6/2009 | Goddard et al. | |
| 2009/0158823 A1 | 6/2009 | Kaduchak et al. | |
| 2009/0162887 A1 | 6/2009 | Kaduchak et al. | |
| 2009/0178716 A1 | 7/2009 | Kaduchak et al. | |
| 2009/0227042 A1 | 9/2009 | Gauer et al. | |
| 2009/0316151 A1 | 12/2009 | Matula et al. | |
| 2010/0000325 A1 | 1/2010 | Kaduchak et al. | |
| 2010/0009333 A1 | 1/2010 | Auer | |

(56) References Cited

U.S. PATENT DOCUMENTS

| | | | |
|---|---|---|---|
| 2011/0024335 A1 | 2/2011 | Ward et al. | |
| 2011/0032522 A1 | 2/2011 | Graves et al. | |
| 2011/0134426 A1 | 6/2011 | Kaduchak et al. | |

FOREIGN PATENT DOCUMENTS

| | | |
|---|---|---|
| CN | 1739020 A | 2/2006 |
| CN | 101060898 | 10/2007 |
| DE | 3027433 | 2/1982 |
| EP | 0 147 032 | 3/1985 |
| EP | 0 292 470 | 11/1988 |
| EP | 0 773 055 | 5/1997 |
| EP | 1 416 239 | 5/2004 |
| FR | 821419 | 12/1937 |
| GB | 500271 | 12/1937 |
| JP | 363139231 | 6/1988 |
| JP | 01-112161 | 4/1989 |
| JP | 406241977 | 9/1994 |
| JP | 07-047259 | 2/1995 |
| JP | 408266891 | 10/1996 |
| JP | 11-014533 | 1/1999 |
| JP | 2002-22531 | 1/2002 |
| RU | 2224992 | 2/2004 |
| WO | WO 88/09210 | 12/1988 |
| WO | WO 90/05008 | 5/1990 |
| WO | WO 94/29695 | 12/1994 |
| WO | WO 97/02482 | 1/1997 |
| WO | WO 99/042810 | 8/1999 |
| WO | WO 00/41794 | 7/2000 |
| WO | WO 02/059577 | 8/2002 |
| WO | WO 02/072234 | 9/2002 |
| WO | WO 02/072236 | 9/2002 |
| WO | WO 03/079006 | 9/2003 |
| WO | WO 2004/024287 | 3/2004 |
| WO | WO 2004/033087 | 4/2004 |
| WO | WO 2004/048948 | 6/2004 |
| WO | WO 2006/031299 | 3/2006 |
| WO | WO 2006/032703 | 3/2006 |
| WO | WO 2006/076195 | 7/2006 |
| WO | WO 2007/128795 | 11/2007 |
| WO | WO 2008/122051 | 10/2008 |
| WO | WO 2009/086043 | 7/2009 |
| WO | WO 2009/091925 | 7/2009 |
| WO | WO 2011/068764 | 6/2011 |

OTHER PUBLICATIONS

Aleksandrov, et al., "Pulsed Laser Florescence Spectrometer," Zhurnal Prikladnoi Spektroskopii, Oct. 1987, 47(4), 686-692.
Anderson, M. et al., "The Physics and Technology of Ultrasonic Particle Separation in Air", WCU, 2003, 1615-1621.
Apfel, R.E. et al., "Acoustic Radiation Pressure—Principles and Application to Separation Science", Fortschritte Der Akustik DAGA'90, 1990, 19-30.
Araz, M.K. et al., "Ultrasonic Separation in Microfluidic Capillaries", IEEE Ultrasonics Symposium, 2003, 1066-1069.
Asai, M.K. et al., "Ultrasonic Treatment of Slurry," Third International Coal Preparation Conference, 1958, 518-527.
Bardsley, et al., "Electroacoustic Productions of Murine Hybridomas," Journal of Immunological Methods, 129(1), 1990, 41-47.
Barmatz, M. et al., "Acosutic radiation potential on a sphere in plane, cylindrical, and spherical standing wave fields", J. Acoust. Soc. Am., 1985, 77, 928-945.
Bauerecker, S. et al., "Formation and growth of ice particles in stationary ultrasonic fields", J. of Chem. Phys., 1998, 3709-3712.
Bazou, D. et al., "Physical Environment of 2-D Animal Cell Aggregates Formed in a Short Pathlength Ultrasound Standing Wave Trap", Ultrasound in Med. & Biol., 2005, 31, 423-430.
Benes, "Separation of Dispersed Particles by Ultrasonic-Induced Coagulation", 15th Conference of the German Society for Acoustics, 1989, 2 pages.
Benes, E. et al., "Improved quartz crystal microbalance technique", J. Appl. Phys., 1984, 56, 608-626.
Beverloo, n. B. et al., "Inorganic Phsophors as New Luminescent Labels for lrnmunocytochernistry and Time-Resolved Microscopy", Cytometry, 1990, 11, 784-792.
Bienvenue, J.M. et al., "Microchip-Based Cell Lysis and DNA Extraction from Sperm Cells for Application to Forensic Analysis", J. Forensic Sci., 2006, 51, 266-273.
Binks, B.P. et al., "Modern Aspects of Emulsion Science", The Royal Society of Chemistry, 1998, 310-321.
Bishop, J.E. et al., "Mechanism of higher brightness of PerCP-Cy5. 5", Cytometry Supp, 2000, 10, 162-163.
Borgnis, "Acoustic Radiation Pressure of Plane Compressional Waves," Reviews of Modern Physics, Jul. 1953, 25(3),653-664.
Borisov, S.M. et al., "Blue LED Excitable Temperature Sensors Based ona New Eurpium (III) Chelate," J. Fluoresc., 2008, 18, 581-589.
Borthwick, K.A. et al., "Development of a novel compact sonicator for cell disruption", J. of Microbioloaical Methods, 2005, 60, 207-216.
Bosma, R. et al., "Ultrasound, a new separation technique to harvest microlalgae", J. Appl. Phycology, 2003, 15, 143-153.
Bossuyt, X. et al., "Comparative Analysis for Whole Blood Lysis Methods for Flow Cytometry", Cytometry, 1997, 30, 124-133.
Brodeur, P. H., "Acoustic Separation in a Laminar Flow," Ultrasonics Symposium, 1994, 1359-1362.
Caperan, P.H. et al., "Acoustic Agglomeration of a Glycol Fog Aerosol: Influence of Particle Concentration and Intensity of the Sound Field at Two Frequencies", J. Aerosol Sci., 1995, 26, 595-612.
Chase, E.S. et al., "Resolution of Dimly Fluorescent Particles: A Practical Measure of Fluorescence Sensitivity", Cytometry, 1998, 33, 267-279.
Cheung, et al., "Impedance Spectroscopy Flow Cytometry: On-Chip Label-Free Cell Differentiation," Cytometry Part A, Feb. 10, 2005, 65A, 124-132.
Coakley, W.T. et al., "Cell-cell contact and membrane spreading in an ultrasound trap", Colloids and Surfaces B: Biointerfaces, 2004, 34, 221 -230.
Coakley, W.T. et al., "Ultrasonic separations in analytical biotechnology", Tibtech, 1997, 15, 506-511.
Coakley, W.T. et al., "Analytical scale ultrasonic standing wave manipulation of cells and microparticles", Ultrasonics, 2000, 38, 638-641.
Condrau, M.A. et al., "Time-Resolved Flow Cytometry for the Measurement of Lanthanide Chelate Fluorescence: I. Concept and Theoretical Evaluation", Cytometry, 1994, 16, 187-194.
Condrau, M.A. et al., "Time-Resolved Flow Cytometry for the Measurement of Lanthanide Chelate Fluorescence: II. Instrument Design and Experimental Results", Cytometry, 1994, 16, 195-205.
Cousins, C.M. et al., "Plasma Preparation from Whole Blood Using Ultrasound", Ultrasound in Med. & Biol., 2000, 26, 881-888.
Curtis, H.W. et al., "Ultrasonic Continuous Flow Plasmapheresis Separator", IBM Tech. Disc. Bulletin, 1982, 25,192-193.
Czyz, H. et al., "On the Concentration of Aerosol Particles by Means of Drift Forces in a Standing Wave Field", Acustica, 1990, 70, 23-28.
Dain, Y. et al., "Dynamics of Suspended Particles in a Two-Dimensional High-Frequency Sonic Field", J. Aerosol Sci., 1995, 26, 575-594.
Dain, Y. et al., "Side drift of aerosols in two-dimensional resonant acoustic levitators", J. Acoust. Soc. Am, 1997, 102, 2549-2555.
Danilov, S D. et al., "Mean force on a small sphere in a sound field in a viscous fluid", J. Acoust. Soc. Am., 2000, 107, 143-1 53.
Danilov, S.D. et al., "The Mean Force Acting on a Small Body in an Axisymmetric Sound Field in a Real Medium", Izvestiva Adademii Nauk Sssr, Mekhanika Zhidkosti I Gaza, 1985, 5, 812-820.
Dean, P.N. et al., "Hydrodynamic Orientation of Sperm Heads for Flow Cytometry", Biophys. J., 1978, 23, 7-13.
Doblhoff-Dier, 0. et al., "A Novel Ultrasonic Resonance Field Device for the Retention of Animal Cells", Biotechnol. Prog., 1994, 10, 428-432.
Doinikov, A.A. et al., "Acoustic radiation force on a spherical particle in a viscous heat-conducting fluid. I. General formula", J. Acoust. Soc. Am., 1997, 101, 713-721.

(56) References Cited

OTHER PUBLICATIONS

Doinikov, A.A. et al., "Acoustic radiation force on a spherical particle in a viscous heat-conducting fluid. II. Force on a rigid sphere", *J. Acoust. Soc. Am.*, 1997, 101, 722-730.
Doinikov, A.A. et al., "Acoustic radiation force on a spherical particle in a viscous heat-conducting fluid. III. Force on a liquid drop", *J. Acoust. Soc. Am.*, 1997, 101, 731-740.
Doinikov, A.A. et al., "Acoustic radiation pressure on a rigid sphere in a viscous fluid", *Proc. R. Soc. Lond.*, 1994, 447-466.
Donnert, G. et al., "Major signal increase in fluorescence microscopy through dark-state relaxation", *Nature Methods*, 2007, 4, 81-86.
Doornbos, R.M. et al., "Experimental and Model Investigations of Bleaching and Saturation of Fluorescence in Flow Cytometry", *Cytometry*, 1997, 29,204-214.
Fenniri, H. et al., "Classification of Spectroscopically Encoded Resins by Raman Mapping and Infrared Hyperspectral Imaging", *Journal of Combinatorial Chemistry*, 2006, 8, 192-198.
Fulwyler, M.J. et al., "Hydronamic Orientation of Cells", *Histochem. Cytoche.*, 1977, 7, 781-783.
Gaida, T.H. et al., "Selective Retention of Viable Cells in Ultrasonic Resonance Field Devices", *Biotech. Prog.*, 1996, 12, 73-76.
Gao, X. et al., "Quantum Dot-Encoded Mesoporous Beads with High Brightness and Uniformity: Rapid Readout Using Flow Cytometry", *Anal. Chem.*, 2004, 3, 2406-2410.
Gherardini, L. et al., "A New Immobilisation Method to Arrange Particles in a Gel Matrix by Ultrasound Standing Waves", *Ultrasound in Med. & Biol.*, 2005, 31, 261-272.
Goddard, G.R. et al., "Ultrasonic Concentration in a Line Driven Cylindrical Tube", *Dissertation*, 2004, 1-276.
Goddard, G. et al., "Single Particle High Resolution Spectral Analysis Flow Cytometry", *Cytometry*, 2006, 69A, 842-851.
Goddard, G. et al., "Ultrasonic particle concentration in a line-driven cylindrical tube", *J. Acoust. Soc. Am.*, 2005, 117, 3440-3447.
Goddard, G. et al., "Ultrasonic Particle-Concentration for Sheathless Focusing of Particles for Analysis in a Flow Cytometer", *Cytometry*, 2006, 69, 66-74.
Gonzalez, I. et al., "Precise Measurements of Particle Entertainment in a Standing-Wave Acoustic Field Between 20 and 3500 Hz", *J. Aerosol Sci.*, 2000, 31,1461-1468.
Gor'Kov, L.P. et al., "On the forces acting on a small particle in an acoustical field in an ideal fluid", *Soviet Physics-Doklady*, 1962, 6, 773-775.
Gould, R.K. et al., "Upper sound pressure limits on particle concentration in fields of ultrasonic standing-wave at megahertz frequencies", *Ultrasonics*, 1992, 30, 239-244.
Gould, R.K. et al., "The effects of acoustic forces on small aprticles in suspension", *Proceedings of the 1973 Symposium on Finite Amplitude Wave Effects in Fluids*, Bjorno, L., ed., Pergamon, Guildford, 1974, 252-257.
Groschl, "Automatic frequency control for piezoelectric resonators and their implementation in the acoustic driftwave resonator", Thesis implemented at the Institute for General Physics the Technical University of Vienna, Nov. 1991, 2 pages.
Grossner, M.T. et al., "Single fiber model of particle retention in an acoustically driven porous mesh", *Ultrasonics*, 2003, 41, 65-74.
Grossner, M.T. et al., "Single-Collector Experiments and Modeling of Acoustically Aided Mesh Filtration", *Amer. Inst. Of Chem. Eng.*, 2005, 51, 1590-1598.
Grossner, M.T. et al., "Transport analysis and model for the performance of an ultrasonically enhanced filtration process", *Chem. Ena. Sci.*, 2005, 60, 3233-3238.
Gupta, S. et al., "Acoustically driven collection of suspended particles within porous media", *Ultrasonics*, 1997, 35, 131-139.
Gupta, S. et al., "Fractionation of Mixed Particulate Solids According to Compressibility Using Ultrasonic Standing Wave Fields", *Chem. Eng. Sci.*, 1995, 50, 3275-3284.
Haake, A. et al., "Contactless micromanipulation of small particles by an ultrasound field excited by a vibrating body", *J. Acoust. Soc. Am.*, 2005, 117, 2752-2760.

Haake, A. et al., "Manipulation of Cells Using an Ultrasonic Pressure Field", *Ultrasound in Med. & Biol.*, 2005, 31, 857-864.
Haake, A. et al., "Positioning of small particles by an ultrasound field excited by surface waves", *Ultrasonics*, 2004, 42, 75-80.
Haake, et al., "Positioning, Displacement, and Localization of Cells Using Ultrasonic Forces," Biotechnology and Bioengineering, 92(1), Aug. 10, 2005, 8-14.
Habbersett, R.C. et al., "An Analytical System Based on a Compact Flow Cytometer for DNA Fragment Sizing and Single Molecule Detection", *Cytometry 2004*, 60A,125-134.
Hager, F. et al., "A Summary of All Forces Acting on Spherical Particles in a Sound Field", *Proc. of the Ultrasonic International '91 Conference and Exhibition*, Le Touauet, France, 1991, 1-4.
Hamilton, M.F. et al., "Acoustic streaming generated by standing waves in two-dimensional channels of arbitrary width", *J. Acoust. Soc. Am.*, 2003, 113, 153-160.
Hamilton, M.F. et al., "Linear and nonlinear frequency shifts in acoustical resonators with varying cross sections", *J. Acoust. Soc. Am.*, 2001, 110, 109-119.
Hancock, A., "*Observation of Forces on Microparticles in Acoustic Standing Waves*", Thesis, submitted in partial satisfaction of the reaquirements for the degree of Master of Science in Biomedical Engineering, University of California, Davis, 2001, 1-155.
Harma, H. et al., "Zeptomole detection sensitivity of prostate-specific antigen in a rapid microtitre plate assay using time-resolved fluorescence", *Luminescence*, 2000, 15, 351-355.
Harris, N. R. et al., "A silicon microfluidic ultrasonic separator", *Sensors and Actuators*, 2004, 95, 425-434.
Harrison, B.S. et al., "Near-Infrared Photo- and Electroluminescence of Alkoxy-Substituted Poly (p-phenylene) and Nonconjugated Polymer/Lanthanide Tetraphenylporphyrin Blends", *Chemistry of Materials*, 2004, 16, 2938-2947.
Hatanaka, S-I et al., "Effect of Process Parameters on Ultrasonic Separation of Dispersed Particles in Liquid", *Jpn. J. Adpi. Phvs.*, 1999, 38, 3096-3100.
Hawkes, et al., "Continuous Cell Washing and Mixing Driven by an Unitrsound Standing Wave Within a Microfluidic Channel," Lab Chip, 4, Sep. 27, 2004, 446-452.
Hawkes, J.J. et al., "Force field particle filter, combinin ultrasound standing waves and laminar flow", *Sensors and Actuators B*, 2001, 75, 213-222.
Hawkes, J.J. et al., "Microparticle manipulation in millimetre scale ultrasonic standing wave chambers", *Ultrasonics*, 1998, 36, 925-931.
Hawkes, J.J. et al., "Single half-wavelength ultrasonic particle filter: Predictions of the transfer matrix multilayer resonator model and experimental filtration results", *J. Acoust. Soc. Am.*, 2002, 111, 1259-1266.
Hawkes, J.J. et al., "A laminar flow expansion chamber facilitating downstream manipulation of particles concentrated using an ultrasonic standing wave", *Ultrasonics*, 1998, 36, 901-903.
Hawkes, J.J. et al., "Ultrasonic deposition of cells on a surface", *Biosensors and Bioelectronics*, 2004, 19,1021-1028.
Hemmila, I. et al., "Progress in Lanthanides as Luminescent Probes", *J. Fluoresncence*, 2005, 15, 529-542.
Hertz, H.M. et al., "Standing-wave acoustic trap for nonintrusive positioning of microparticles", *J. Appl. Phys.*, 1995, 78, 4845-4849.
Higashitani, K.O. et al., "Migration of Suspended Particles in Plane Stationary Ultrasonic Field", *Chem. Eng. Sci.*, 1981, 36, 1187-1192.
Hill M. et al., "Modelling in the design of a flow-through ultrasonic separator", *Ultrasonics*, 2000, 38, 662-665.
Hill M. et al., "Modelling of layered resonators for ultrasonic separation", *Ultrasonics*, 2002, 40, 385-392.
Hill, D.H. et al., "Operating Characteristics of Acoustically Driven Filtration Processes for Particulate Suspensions", *Sep. Sci. And Tech.*, 2000, 35, 1363-1375.
Hill, M. M et al., "The selection of layer thicknesses to control acoustic radiation forces profiles in layered resonators", *J. Acoust. Soc. Am.*, 2003, 114(5), 2654-2661.
Hirschfeld, T. et al., "Fluorescence Background Discrimination by Prebleaching", *J. Histochem. and Cytochem.*, 1979, 27, 96-101.
Holmes, D. et al., "High throughput particle analysis: Combining dielectrophoretic particle focussing with confocal optical detection", *Biosensors and Bioelectronics*, 2006, 21, 1621-1630.

(56) References Cited

OTHER PUBLICATIONS

Holwill, I.L. et al., "The use of ultrasonic standing waves to enhance optical particle sizing equipment", *Ultrasonics*, 2000, 38, 650-653.
Huhtinen, P. et al., "Synthesis, Characterization, and Application of Eu(III), Tb(III), Sm (III), and Dy(III) Lanthanide Chelate Nanoparticle Labels", *Anal. Chem.*, 2005, 77, 2643-2648.
Invitrogen, "Fluo-4 NW Calcium Assay Kits (F36205, F36206)", *Product Information*, 2006.
Invitrogen, "Fluorophore selection guide for flow cytometry", *Cellular Analysis*, 2007.
Johnston, P.A. et al., "Cellular platforms for HTS: three case studies", *DDT*, 2002, 7, 353-363.
Jonsson, H. et al., "Particle separation using ultrasound can be used with human shed mediastinal blodd", *Perfusion*, 2005, 20, 39-43.
Juarez, J.A. et al., "Piezoelectric Transducer for Air-Borne Ultrasound", *Acustica*, 1973, 29, 234-239.
Kaduchak, G. et al., "E6 diffraction catastrophe of the primary rainbow of oblate water drops: observations with white-light and laser illumination", *Applied Optics*, 1994, 33, 4691-4696.
Kaduchak, G. et al., "Hyperbolic umbilic and E6 diffraction catastrophes associated with the secondary rainbow of oblate water drops: observations with laser illumination", *Applied Optics*, 1994, 33, 4697-4701.
Kapishnikov, S. et al., "Continuous particle size separation and size sorting using ultrasound in a microchannel", *J. Stat. Mech.*, 2006, 1-13.
Karumanchi, R.S. et al., "Field-assisted extraction of cells, particles and macromolecules", *TRENDS is Biotech*, 2002, 20, 72-78.
Kaye, P.H. et al., "Spatial light-scattering analysis as a means of characterizing and classifying non-spherical particles", *Meas. Sci. Technol.*, 1998, 9, 141-149.
Keij, et al., "Coincidence in High-Speed Flow Cytometry: Models and Measurements," Cytometry 12, Jan. 22, 1991, 398-404.
Kilburn, D.G. et al., "Enhanced Sedimentation of Mammalian Cells following Acoustic Aggregation", *Biotech. And Bioeng.*, 1989, 34, 559-562.
King, L.V. et al., "On the acoustic radiation on spheres", *Proc. R. Soc. A.*, 1933, 147, 212-240.
Kogan, S. et al., "Acoustic concentration of particles in piezoelectric tubes: Theoretical modeling of the effect of cavity shape and symmetry breaking", *J. Acoust. Soc. Am.*, 2004, 116, 1967-1974.
Kozuka, T. et al., "Acoustic Micromanipulation Using a Multi-Electrode Transducer", *7th Inter. Svmp. On Micro Machine and Human Science IEEE*, 1996, 163-170.
Kozuka, T. et al., "Control of a Standing Wave Field Using a Line-Focused Transducer for Two-Dimensional Manipulation of Particles", *Jpn. J. Appl. Phys.*, 1998, 37, 2974-2978.
Kozuka, T. et al., "Micromanipulation Using a Focused Ultrasonic Standing Wave Field", *Electronics and Communications in Japan*, 2000, Part 3, 83(1), 1654-1659.
Kumar, M. et al., "Fractionation of Cell Mixtures Using Acoustic and Laminar Flow Fields", *Biotech. Bioeng.*, 2005, 89, 129-137.
Kundt, A. et al., "Longitudinal vibrations and acoustic figures in cylindrical columns of liquids", *Annalen der Physik and Chemie (Poggendorff's Annalen)*, 1874, 153, 1-12.
Kuznetsova, L.A. et al., "Cavitation buble-driven cell and particle behavior in a ultrasound standing wave", *J. Acoust. Soc. Am.*, 2005, 117, 104-112.
Kuznetsova, L.A. et al., "Microparticle concentration in short path length ultrasonic resonators: Roles of radiation pressure and acoustic streaming", *J. Acoust. Soc. Am.*, 2004, 116, 1956-1966.
Kwiatkowski, C.S. et al., "Resonator frequency shift due to ultrasonically induced microparticle migration in an aqueous suspension: Observations and model for the maximum frequency shift", *J. Acoust. Soc. Am.*, 1998, 103, 3290-3300.
Lakowicz, J.R. et al., "On the Possibility of Long-Wavelength Long-Lifetime High-Quantum-Yield Luminophores", *Analytical Biochemistry*, 2001, 288, 62-75.
Leif, R.C. et al., "Increasing the Luminescence of Lanthanide Complexes", *Cytometry*, 2006, 69A, 767-778.
Leif, R.C. et al., "Markers for Instrumental Evaluation of Cells of the Female Reproductive Tract; Existing and New Markers", in *The Automation of Uterine Cancer Cytology Tutorials of Cytology*, (edited by G.L. Wied. et al.), 1976, 313-344.
Lierke, E.G. et al., "Acoustic Positioning for Space Processing of Materials Science Samples in Mirror Furnaces", *IEEE Ultrasonics Symposium*, 1983, 1129-1139.
Lilliehorn, T. et al., "Trapping of microparticles in the rear field of an ultrasonic transducer", *Ultrasonics*, 2005, 43, 293-303.
Lofstedt, R. et al., "Theory of long wavelength acoustic radiation pressure", *J. Acoust. Soc. Am.*, 1991, 90, 2027-2033.
Loken, M.R. et al., "Cell Discrimination by Multiangle Light Scattering", *Histochem. Cytochem.*, 1976, 24, 284-291.
Loken, M.R. et al., "Identification of Cell Asymmetry and Orientation by Light Scattering", *Histochem. Cytochem.*, 1977, 7, 790-795.
Macey, M.G. et al., "Comparative Study of Five Commercial Reagents for Preparing Normal and Leikaemic Lymphoctyes for Immunophenotypic Analysis by Flow Cytometry", *Cytometry*, 1999, 38,153-160.
Maltsev, V.P. et al., "Scanning flow cytometry for individual particle analysis", *Review of Scientific Instruments*, 2000, 71, 243-255.
Mandralis, Z. et al., "Enhanced synchronized ultrasonic and flow-field fractionation of suspensions", *Ultrasonics*, 1994, 32, 113-121.
Mandralis, Z. et al., "Transient Response of Fine Particle Suspensions to Mild Planar Ultrasonic Fields", *Fluid/Particle Separation J.*, 1990, 115-121.
Marston, P.L. et al., "Generalized rainbows and unfolded glories of oblate drops: organization for multiple internal reflection and extension of cusps into Alexander's dark band", *Applied Optics*, 1994, 33, 4702-4713.
Marston, P.L. et al., "Manipulation of Fluid Objects with Acoustic Radiation Pressure", *Ann. N. Y. Acad. Sci.*, 2004, 1027, 414-434.
Marston, P.L., "Tensile Strength and Visible Ultrasonic Cavitation of Superfluid 4He*," Journal of Low Temperature Physics, 25(3/4), Mar. 5, 1976, 383-407.
Marston, P.L. et al., "Resonances, Radiation Pressure, and Optical Scattering Phenomena of Drops and Bubbles", *Proceedings of the Second International Colloquium on Drops and Bubbles, Jet Prop. Lab. Pub 82-7* Pasadena, CA, 1982, 166-174.
Martin, K.M. et al., "Acoustic filtration and sedimentation of soot particles", *Experiments in Fluids*, 1997, 23, 483-488.
Masudo, T. et al., "Particle Characterization and Separation by a Coupled Acoustic-Gravity Field", *Analytical Chemistry* 2001, 73, 3467-3471.
Mathies, R.A. et al., "Optimization of High-Sensitivity Fluorescence Detection", *Anal. Chem.*, 1990, 62, 1786-1791.
Mazumdar, M.K. et al., "Spart Analyzer: Its Application to Aerodynamic Size Distribution Measurement", *J. Aerosol Sci.*, 1979, 10, 561-569.
Mazumdar, M.K. et al., "Single particle aerodynamic relaxation time analyzer", *Rev. Sci. Instrum.*, 1977, 48, 622-624.
McCartin, B.J., "A Numerical Procedure for 2D Acoustic Waveguides with Heated Walls", http://flux.aps.org/meetings/YR99/OSS99/abs/S700004.html, 1999.
Meindersma, G.W. et al., "Separation of a biocatalyst with ultrafiltration or filtration after bioconversion", *J. Membrane Sci.*, 1997, 125, 333-349.
Morgan, J. et al., "Manipulation of in vitro toxicant sensors in an ultrasonic standing wave", *Toxicology in Vitro*, 2004, 18, 115-120.
Mullaney, P.F, et al., "The Small Angle Light Scattering of Biological Cells", *Biophys. J.*, 1970, 10, 764-772.
Neild, A., "A micro-particle positioning technique combining an ultrasound manipulator and a microgripper," *J. Micromechanical Microengineering*, 2006, 16, 1562-1570.
Neild, A. et al., "Design, modeling and characterization of microfluidic devices for ultrasonic manipulation", *Sensors and Actuators B: Chemical*, Feb. 20, 2007, 121(2).
Neukammer, J. et al., "Angular distribution of light scattered by single biological cells and oriented particle agglomerates", *Appl. Opt.*, 2003, 42, 6388-6397.
Nilsson, A. et al., "Acoustic control of suspended particles in micro fluidic chips", *Lab Chip*, 2004, 4, 131-135.

(56) References Cited

OTHER PUBLICATIONS

Nolan et al., "Suspension Array Technology: New Tools for Gene and Protein Analysis", *Cell and Molecular Biology*, 2001, 47, 1241-1256.
Nowotny, H. et al., "Layered piezoelectric resonators with an arbitrary No. electrodes (general one-dimensional treatment)", *J. Acoust. Soc. Am.*, 1991, 90, 1238-1245.
Otaki, M. et al., "Virus Removal in a Membrane Separation Process", *Water Sci. and Tech.*, 1998 37, 107-116.
Pangu, G.D. et al., "Acoustically aided separation of oil droplets from aqueous emulsions", *Chem. Eng. Sci.*, 2004, 59, 3183-3193.
Petersson et al., "Separation of Lipids from Blood Utilizing Ultrasonic Standing Waves in Microfluidic Channels," *Analyst*, 2004, 129, 938-943.
Petersson, F., "Particle Flow Switch Utilizing Ultrasonic Particle Switching in Microfluidic Channels", *7th International Conf on Miniaturizing Chem and Biochem Analysis Systems*, 2003, 879-882.
Petersson, F. et al., "Continuous separation of lipid particles from erythrocytes by means of laminar flow and acoustic standing wave forces", *Lab Chip*, 2005, 5, 20-22.
Petersson, F. et al., "Carrier Medium Exchange through Ultrasonic Particle Switching in Microfluidic Channels", *Anal. Chem.*, 2005, 77, 1216-1221.
Petersson, F. et al., "Free Flow Acoustophoresis: Microfluidic-Based Mode of Particle and Cell Separation", *Anal. Chem.*, 2007 79, 5117-5123.
Pregibon, D.C. et al., "Multifunctional Encoded Particles for High-Throughput Biomolecule Analysis", *Science*, 2007, 315, 1393-1396.
Princen, K. et al., "Evaluation of SDF-1/CXCR4-Induced Ca2+Signaling by Fluorometric Imaging Plate Reader (FLIPR) and Flow Cytometry", *Cytometry*, 2003, 51A, 35-45.
Pui, P.W. et al., "Batch and Semicontinuous Aggregattion and Sedimentation of Hybridoma Cells by Acoustic Resonance Fields", *Biotechnol. Prog.*, 1995, 11, 146-152.
Rama Rao, G.V. et al., "Monodisperse Mesoporous Silica Microspheres Formed by Evaporation-Induced Self Assembly of Surfacant Templates in Aerosols", *Advanced Materials*, 2002, 18,1301 -1304.
Rens, W. et al., "A Novel Nouel for More Efficient Sperm Orientation to Improve Sorting Efficiency of X and Y Chromosome-Bearing Sperm", *Cytometry*, 1998, 33, 476-481.
Ricks, D.C. et al., "A numerically stable global matrix method for cylindrically layered shells excited by ring forces", *J. Acoust. Soc. Am.*, 1994, 95, 3339-3349.
Rouleau, F. et al., "Electromagnetic scattering by compact clusters of spheres", *Astron. Astrophys*, 1996, 310, 686-698.
Rudnick, J. et al., "Oscillational instabilities in single-mode acoustic levitators", *J. Acoust. Soc. Am.*, 1990, 87, 81-92.
Saito, M. et al., "Microorganism manipulation and microparticle arrangement by the use of ultrasonic standing waves", *SPIE*, 2001, 4590, 26-37.
Saito, M. et al., "Ultrasonic manipulation of locomotive microorganisms and evaluation of their activity", *J. App. Physics*, 2002, 92, 7581-7586.
Saito, M. et al., "Ultrasonic trapping of paramecia and estimation of their locomotive force", *Appl. Phys. Lett*,1997, 71,1909-1911.
Saito, M. et al., "Ultrasonic waves for fabricating lattice structure in composite materials", *SPIE*, 1999, 3786, 179-190.
Saito, M. et al., "Quantum mechanical representation of acoustic streaming and acoustic radiation pressure", *Physical Review*, 2001, E64, 026311-1-026311-5.
Samiotaki, M. et al., "Seven-Color Time-Resolved Fluorescence Hybridization Analysis of Human Papilloma Virus Types", *Analytical Biochem.*, 1997, 253, 156-161.
Schmid, M. et al., "A computer-controlled system for the measurement of complete admittance spectra of piezoelectric resonators", *Meas. Sci. Technol.*, 1990, 1, 970-975.
Schoell, W.M. et al., "Separation of Sperm and Vaginal Cells with Flow Cytometry for DNA Typing After Sexual Assault", *Obstetrics and Gynecolony*, 1999, 94, 623-627.

Semianov, K.A. et al., "Measurement of Mammalian Erythrocyte Indices from Light Scattering with Scaning Flow Cytometer", *Proc. SPIE*, 2003, 5141,106-113.
Sethu, P. et al., "Continuous Flow Microfluidic Device for Rapid Erythrocyte Lysis", *Anal. Chem.*, 2004, 76, 6247-6253.
Shapiro, H.M. et al., *Practical Flow Cytometry*, Hoboken, NJ, John Wiley & Sons. Inc., 2005, 9-13.
Shvalov, A.N. et al., "Individual *Escherichia coli* Cells Studied from Light Scattering with the Scanning Flow Cytometer", *Cytometry*, 2000, 41, 41-45.
Shvalov, A.N. et al., "Light -scattering properties of individual erythrocytes", *Applied Optics*, 1999, 38, 230-235.
Simpson, H.J. et al., "Ultrasonic four-wave mixing mediated by an aqueous suspension of microspheres: Theoretical steady-state properties", *J. Acoust. Soc. Am.*, 1995, 98, 1731-1741.
Skudrzyk, E. et al., "Die Grundlagen der Akustik", *Sprinaer Verlaa. Wien*, 1954, 202-205 and 807-825.
Slomkowski, S. et al., "New Types of Microspheres and Microsphere-related Materials for Medical Diagnostics", *Polymers for Advanced Technologies*, 2002, 13, 906-918.
Sobanski, M.A. et al., "Sub-micron particle manipulation in an ultrasonic standing wave: Applications in detection of clinically important biomolecules", *Bioseparation*, 2001, 9, 351-357.
Steinkamp, J.A., "A Differential Amplifier Circuit for Reducing Noise in Axial Light Loss Measurements", *Cyometry*, 1983, 4, 83-87.
Steinkamp, J.A. et al., "Dual-Laser, Differential Fluorescence Correction Method for Reducing Cellular Background Autofluorescence", *Cytometry*,1986, 7, 566-574.
Steinkamp, J.A. et al., "Enhanced Immunofluorescence Measurement Resolution of Surface Antigens on Highly Autofluorescent, Glutaraldehyde-Fixed Cells Analyzed by Phase-Sensitive Flow Cytometry", *Cytometry*, 1999, 37, 275-283.
Stewart, C.C. et al., "Resolving Leukocytes Using Axial Light Loss", *Cytometry*, 1989, 10, 426-432.
Stoffel, C.L. et al., "Data Analysis for a Dual Analysis for a Dual-Channel Virus Counter", *Analytical Chemistry*, 2005, 77, 2243-2246.
Stoffel, C.L. et al., "Design and Characterization of a Compact Dual Channel Virus Counter", *Cytometry*, 2005, Part A 65A, 140-147.
Stove!, R.T. et al., "A Means for Orienting Flat Cells in Flow Systems", *Biophys J.*, 1978, 23, 1-5.
Takeuchi, M. et al., "Ultrasonic Micromanipulation of Small Particles in Liquid", *Jpn J. Appl. Phys.*, 1994, 33, 3045-3047.
Takeuchi, J. et al., "Ultrasonic Micromanipulator Using Visual Feedback", *Jpn J. Appl. Phys.*, 1996, 35, 3244-3247.
Thiessen, D.B. et al., "Principles of some Acoustical, Electrical, and Optical Manipulation Methods with Applications to Drops, Bubbles, and Capillary Bridges", *ASME Fluids Eng. Div. Publ. FED*, 1998.
Thiessen, D.B. et al., "Some Responses of Small Diffusion Flames to Ultrasonic Radiation", *NASA*, 2003, 321-324.
Tolt, T. L. et al., "Separation devices based on forced coincidence response of fluid-filled pipes", *J. Acoust. Soc. Am.*, 1992, 91, 3152-3156.
Tolt, T.L. et al., "Separation of Dispersed Phases from Liquids in Acoustically Driven Chambers", *Chem. Eng. Science*, 1993, 48, 527-540.
Townsend, R.J. et al., "Modelling of particle paths passing through an ultrasonic standing wave", *Ultrasonics*, 2004, 42, 319-324.
Trihn, E.H. et al., "Experimental study of streaming flows associated with ultrasonic levitators", *Phys. Fluids*, 1994, 6, 3567-3579.
Trinh, E.H. et al., "Compact acoustic levitation device for studies in fluid dynamics and material science in the laboratory and microgravity", *Rev. Sci. Instrum.*, 1985, 56, 2059-2065.
Tuckermann, R. et al., "Trapping of heavy gases in stationary ultrasonic fields", *Chem. Phys. Ltrs.*, 2002, 363, 349-354.
Tung, Yi-C. et al., "PDMS-based opto-fluidic micro flow cytometer with two-color, multi-angle fluorescence detection capability using PIN photodiodes", *Sensors and Actuators*, 2004, 98, 356-367.
Tyson, D.S. et al., "Ruthenium (II) complex with a notably long excited state lifetime", *The Royal Society of Chemistry*, 2000, 2355-2356.
Vainshtein, P. et al., "On the Drift of Aerosol Particles in Sonic Fields", *J. Aerosol Sci.*, 1992, 23, 631-637.

(56) References Cited

OTHER PUBLICATIONS

Vainshtein, P. et al., "The effect of centreline particle concentration in a wave tube", *J. Fluid Mech.*, 1996, 306, 31-42.

Van Hee, P. et al., "Strategy for Selection of Methods for Separation of Bioparticles From Particle Mixtures", *Biotech. Bioeng.*, 2006, 94, 689-709.

Verpoorte, E. et al., "Beads and chips: new recipes for analysis—Elisabeth Verpoorte reviews particle handling in microchannels", *Lab Chip*, 2003, 3, 60N-68N.

Visuri, S.V. et al., "Microfluidic tolls for biological sample preparation", *Poster 1423, 2nd Annual International IEEE-EMBS Special Topic Cofnerence on Microtechnologies in Medicine & Biology*, May 2-24, 2002, 556-559.

Wang, Z. et al., "Retention and Viability Characteristics of Mammalian Cells in an Acoustically Driven Polymer Mesh", *Biotechnol. Prog.*, 2004, 20, 384-387.

Ward, M. et al., "Manipulation of Immunomagnetic Targets in Microfluidic Channel Flow", *Dissertation*, 2005, 1-205.

Weiser, M.A. et al., "Interparticle Forces on Red Cells in a Standing Wave Field", *Acustica*, 1984, 56, 114-119.

Weiser, M.A.H. et al., "Extension of acoustic levitation to include the study of micron-size particles in a more compressible host liquid", *J. Acoust. Soc. Am.*, 1982, 71, 1261-1268.

Whitworth, G. et al., "Particle col. formation in a stationary ultrasonic field", *J. Acoust. Soc. Am.*, 1992, 91, 79-85.

Whitworth, G. et al., "Transport and harvesting of suspended particles using modulated ultrasound", *Ultrasonics*, 1991, 29, 439-444.

Wu, Y. et al., "Diazo Coupling Method for Covalent Attachment of Proteins to Solid Substrates", *Bioconjugate Chem.*, 2006, 17, 359-365.

Yagi, et al., "Flow Cytometry to Evaluate *Theileria Sergenti Parasitemia* Using the Florescent Nucleic Acid Stain SYTO16," *Cytometry*, 2000, 41, 223-225.

Yamakoshi, Y. et al., "Micro particle trapping by opposite phases ultrasonic travelling waves", *Ultrasonics*, 1998, 36, 873-878.

Yasuda, K. et al., "Concentration and Fractionation of Small Particles in Liquid by Ultrasound", *Jpn J. Appl. Phys.*, 1995, 34, 2715-2720.

Yasuda, K. et al., "Deoxyribonucleic acid concentration using acoustic radiation force", *J. Acoust. Soc. Am.*, 1996, 99, 1248-1251.

Yasuda, K. et al., "Non-destructive, non-contact handling method for biomaterials in micro-chamber by ultrasound", *Sensors and Actuators*, 2000, 64, 128-135.

Yasuda, K. et al., "Particle separation using acoustic radiation force and elecrostatic force", *J. Acoust. Soc. Am.*, 1996, 99, 1965-1970.

Yasuda, K. et al., "Blood Concentration by Superposition of Higher Harmonics of Ultrasound", *Jpn. J. Appl. Phys.*, 1997, 36, 3130-3135.

Yasuda, K. et al., "Using acousitc radiation force as a concentration method for erythrocytes", *J. Acoust. Soc. Am.*, 1997, 102, 642-645.

Ye, C-H. et at., "Preparation of three terbium complexes with paminobenzoic acid and investigation of crystal structure influence on luminescence property", *Journal of Solid State Chemistry*, 2004, 177, 3735-3742.

Yosioka, K. et al., "Acoustic Radiation Pressure on a Comressible Sphere", *Acustica*, 1955, 5, 167-173.

Yuan, J. et al. "Lanthanide-based luminescence probes and time-resolved luminescence bioassays", *Trends in Analytical Chemistry*, 2006, 25, 490-500.

Yurkin, M.A. et al., "Experimental and theoretical study of light scattering by individual mature red blook cells by use of scanning flow cytometry and a discrete dipole approximation", *Applied Optics*, 2005, 44, 5249-5256.

EPO Application No. EP 08733084: Extended European Search Report dated Mar. 24, 2010.

Response to Mar. 24, 2010 Extended European Search Report in European Application No. 08733084.1 filed Jun. 16, 2010.

International Application No. PCT/US05/26524: International Search Report dated Oct. 3, 2006.

International Application No. PCT/US08/87579: International Search Report dated Feb. 9, 2009.

International Application No. PCT/US08/87579, Written Opinion dated Feb. 9, 2009.

International Application No. PCT/US08/87579, Written Opinion dated Jul. 26, 2010.

International Application No. PCT/US2008/059181: International Search Report dated Jul. 25, 2008.

International Application No. PCT/US2009/031154: International Search Report dated Jul. 8, 2009.

U.S. Appl. No. 11/982,042: Restriction Requirement dated Nov. 30, 2009.

U.S. Appl. No. 11/982,042: Non-Final Office Action dated Jun. 10, 2010.

U.S. Appl. No. 11/982,042: Final Office Action dated Sep. 24, 2010.

U.S. Appl. No. 11/982,042: Non-Final Office Action dated Mar. 4, 2011.

U.S. Appl. No. 11/593,312: Non-Final Office Action dated Oct. 16, 2008.

U.S. Appl. No. 11/593,312: Final Office Action dated May 13, 2009.

U.S. Appl. No. 11/593,312: Non-Final Office Action dated Oct. 23, 2009.

U.S. Appl. No. 11/593,312: Final Rejection dated Apr. 5, 2010.

U.S. Appl. No. 11/593,312: Notice of Allowance dated Jul. 6, 2010.

U.S. Appl. No. 11/593,312: Notice of Allowance dated Sep. 16, 2010.

U.S. Appl. No. 11/784,936: Non-Final Office Action dated Apr. 3, 2008.

U.S. Appl. No. 11/784,936: Final Office Action dated Dec. 31, 2008.

U.S. Appl. No. 11/784,936: Non-Final Office Action dated Jun. 24, 2009.

U.S. Appl. No. 11/784,936: Notice of Allowance dated Feb. 22, 2010.

U.S. Appl. No. 11/784,936: Notice of Allowance dated May 28, 2010.

U.S. Appl. No. 11/784,936: Notice of Allowance dated Sep. 16, 2010.

U.S. Appl. No. 12/283,491: Restriction Requirement dated Jun. 25, 2010.

U.S. Appl. No. 12/283,491: Non-Final Office Action dated Sep. 27, 2010.

U.S. Appl. No. 12/283,491: Final Office Action dated Apr. 5, 2011.

U.S. Appl. No. 12/283,461: Restriction Requirement dated Jun. 28, 2010.

U.S. Appl. No. 12/283,461: Non-Final Office Action dated Sep. 28, 2010.

U.S. Appl. No. 12/283,461: Final Office Action dated Apr. 5, 2011.

U.S. Appl. No. 12/903,003: Non-Final Office Action dated Nov. 15, 2010.

U.S. Appl. No. 12/903,003: Final Office Action dated Jun. 23, 2011.

U.S. Appl. No. 11/982,042: Final Office Action dated Oct. 17, 2011.

U.S. Appl. No. 11/784,928: Restriction Requirement dated Jul. 1, 2009.

U.S. Appl. No. 11/784,928: Non-Final Office Action dated Dec. 30, 2009.

U.S. Appl. No. 11/784,928: Final Rejection dated Jul. 7, 2010.

U.S. Appl. No. 11/784,928: Notice of Allowance dated Dec. 13, 2010.

U.S. Appl. No. 12/283,491: Non-Final Office Action dated Sep. 27, 2011.

U.S. Appl. No. 12/283,461: Non-Final Office Action dated Sep. 26, 2011.

U.S. Appl. No. 12/903,003: Non-Final Office Action dated Oct. 24, 2011.

U.S. Appl. No. 12/903,003: Final Office Action dated Feb. 6, 2012.

U.S. Appl. No. 12/903,042: Non-Final Office Action dated Nov. 15, 2012.

U.S. Appl. No. 12/903,003: Non-Final Office Action dated Feb. 13, 2013.

U.S. Appl. No. 12/283,491: Ex parte Quayle Action dated Mar. 29, 2012.

U.S. Appl. No. 12/283,491: Notice of Allowance dated May 25, 2012.

U.S. Appl. No. 12/283,461: Ex parte Quayle Action dated Mar. 29, 2012.

U.S. Appl. No. 12/283,461: Notice of Allowance dated May 31, 2012.

U.S. Appl. No. 12/903,003: Non-Final Office Action dated Jun. 19, 2012.

U.S. Appl. No. 12/903,003: Final Office Action dated Oct. 24, 2012.

(56) References Cited

OTHER PUBLICATIONS

U.S. Appl. No. 12/903,042: Non-Final Office Action dated May 11, 2012.
U.S. Appl. No. 11/982,042: Non-Final Office Action dated Oct. 22, 2013.
U.S. Appl. No. 13/966,624: Non-Final Office Action dated Sep. 24, 2013.
U.S. Appl. No. 13/571,629: Restriction Requirement dated Dec. 6, 2013, 10 pages.
U.S. Appl. No. 13/618,237: Non-Final Office Action dated Jan. 27, 2014, 13 pages.
U.S. Appl. No. 13/966,624: Final Office Action dated Jan. 28, 2014, 15 pages.
U.S. Appl. No. 12/903,042: Final Office Action dated May 24, 2013.
U.S. Appl. No. 12/903,042: Non-Final Office Action dated Sep. 18, 2013.
U.S. Appl. No. 13/618,237: Restriction Requirement dated Sep. 3, 2013.
Anderson, M.J. et al., "Use of Acoustic Radiation Pressure to Concentrate Small Particles in an Air Flow," 2002 IEEE Ultrasonics Symposium, Jan. 1, 2002, 481-484.
U.S. Appl. No. 12/903,003: Notice of Allowance dated Jun. 5, 2013.

\* cited by examiner

APPARATUS FOR SEPARATING PARTICLES UTILIZING ENGINEERED ACOUSTIC CONTRAST CAPTURE PARTICLES

CROSS REFERENCE TO RELATED APPLICATIONS

This application is a continuation of U.S. patent application Ser. No. 11/784,928, filed Apr. 9, 2007, the contents of which is incorporated by reference herein in its entirety.

STATEMENT OF GOVERNMENT INTEREST

This invention was made with Government support under Contract Number DE-AC51-06NA25396 awarded by the United States Department of Energy. The Government has certain rights in the invention.

TECHNICAL FIELD

The present invention relates, in general, to field-based separation of particles in a medium utilizing acoustic pressure.

BACKGROUND

It was realized early in ultrasonic transport phenomena that particles with different mechanical properties (density and compressibility) can be separated in a solution. Particles in an ultrasonic standing wave field that are more dense and less compressible than the background medium are transported to a different spatial location than particles that are less dense and more compressible than the background medium, producing a true binary separator based upon mechanical properties. Ultrasonic radiation pressure has been demonstrated as a viable means to manipulate and locally trap particles in microfluidic environments. In application, the acoustic radiation pressure force depends upon frequency of excitation, pressure amplitude within the medium, and the density/compressibility contrast between the particle of interest and the host medium. Within an applied ultrasonic standing wave, particles experience a drift force resulting from acoustic radiation pressure that transports the particles to a position within the applied standing wave that corresponds to minima in the acoustic radiation pressure force potential. In general, the location of this minima is located in a different spatial location for particles that are more dense and less compressible than the background medium in comparison to particles that are less dense and more compressible. The technique has been successfully demonstrated in particle conditioning experiments involving trajectory steering, agglomeration, retainment, mixing, selective retainment and deposition of cells on a surface.

Separation utilizing acoustic radiation pressure has not been readily implemented in biological problems since most biological particles of interest (e.g. red blood cells, white blood cells, bacteria, spores, etc.) all are more dense and less compressible than water. Recent biological assays have implemented means to separate analytes from sample solutions by taking advantage of their physical properties. For instance, positively charged silica surfaces are used to capture highly negative charged DNA molecules from complex samples. More recently, capture particles have been employed to capture biological particles of interest. This has been especially true for magnetic field-base purification methods where magnetic particles are used to capture particles of interest from within a sample and then separated from the sample using magnetic fields.

It is desirable, therefore, to provide an apparatus and method for separating particles within a medium utilizing engineered capture particles and acoustic radiation pressure.

SUMMARY

An apparatus and a method for separating particles from a medium includes a capillary defining a flow path therein that is in fluid communication with a medium source. The medium source includes engineered acoustic contrast capture particle having a predetermined acoustic contrast. The apparatus includes a vibration generator that is operable to produce at least one acoustic field within the flow path. The acoustic field produces a force potential minima for positive acoustic contrast particles and a force potential minima for negative acoustic contrast particles in the flow path and drives the engineered acoustic contrast capture particles to either the force potential minima for positive acoustic contrast particles or the force potential minima for negative acoustic contrast particles.

The engineered acoustic contrast capture particles may have a negative acoustic contrast and may have a density/compressibility ratio less than that of the medium source. Alternatively, the engineered acoustic contrast capture particles may have a positive acoustic contrast and may have a density/compressibility ratio greater than that of the medium source.

Alternatively, the medium source includes particles having positive acoustic contrast and particles having negative acoustic contrast and the acoustic field drives the positive acoustic contrast particles to the potential minima for positive acoustic contrast particles and the negative acoustic contrast particles to the potential minima for negative acoustic contrast particles. The positive acoustic contrast particles may be bioparticles. The force potential minima for positive contrast particles may be a pressure node and the force potential minima for negative contrast particles may be a pressure antinode.

Alternatively, the engineered acoustic contrast capture particles are functionalized to bind to corresponding targets in the medium. The engineered acoustic contrast capture particles may bind to the targets with antibodies. The targets may be biological molecules or particles. The vibration generator may be a transducer or a line-drive element.

Alternatively, the acoustic field is a dipole acoustic field and the force potential minima for positive acoustic contrast particles may be located along a center of the flow path and the force potential minima for negative acoustic contrast particles may be located adjacent a wall of the capillary. Alternatively, the acoustic field is an axisymmetric acoustic field and the force potential minima for negative acoustic contrast particles may be located along a center of the flow path and the force potential minima for positive acoustic contrast particles may be located adjacent a wall of the capillary.

Alternatively, the capillary is an inner capillary disposed within an outer capillary and the vibration generator may be disposed adjacent the outer capillary. The capillary may be quartz, glass, or plastic. The apparatus may further comprise a laser beam for analysis of the particles in the medium. The vibration generator may be capable of alternately producing a dipole acoustic field and an axisymmetric acoustic field.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF ILLUSTRATIVE EMBODIMENTS

The acoustic radiation pressure force on a compressible, spherical particle of volume V in an arbitrary acoustic field can be written in terms of an acoustic radiation pressure force potential U:

$$U = \frac{4}{3}\pi a^3 \left[ \left(\beta_o \frac{\langle p^2 \rangle}{2}\right) f_1 - \frac{3}{2}\left(\frac{\rho_o \langle v^2 \rangle}{2}\right) f_2 \right]$$

Here, a is the particle radius, $\beta_o$ is the compressibility of the surrounding fluid, and $\rho_o$ is the density of the surrounding fluid. The pressure and velocity of the acoustic field in the absence of the particle are described by p and v, respectively, and the brackets correspond to a time-averaged quantity. The terms $f_1$ and $f_2$ are the contrast terms that determine how the mechanical properties of the particle differ from the background medium. They are given by:

$$f_1 = 1 - \frac{\beta_p}{\beta_o}$$

$$f_2 = \frac{2(\rho_p - \rho_o)}{(2\rho_p - \rho_o)}$$

The subscript p corresponds to intrinsic properties of the particle. The force F acting on a particle is related to the gradient of the force potential by:

$$F = -\Delta U$$

Particles will be localized at positions where the potential U displays a minima.

For acoustic wavefields comprised of plane waves, the potential minima of U occur at either pressure nodes or antinodes depending upon the signs of $f_1$ and $f_2$. Most particles and cells of interest in a water or aqueous background medium have properties that yield positive values of $f_1$ and $f_2$. These particles are termed positive acoustic contrast particles. Under the plane wave approximation, these particles will migrate to the pressure nodes (velocity antinodes) in the system. Examples of these particles in water-based buffers include erythrocytes, leukocytes, bacteria, yeast, or any other particles where density and compressibility contrast terms $f_1$ and $f_2$ are positive. Materials such as fat globules and gas bubbles yield negative values of both $f_1$ and $f_2$ and are termed negative contrast particles. Under the plane wave approximation, these particles will move to the location of a pressure antinode. This system can be used as a binary particle separator that spatially localizes particles into discrete locations in the wavefield (pressure nodes or antinodes) based upon positive or negative acoustic contrast of the particles relative to the background medium.

When the wavefield takes on greater complexity than described by plane wave approximations (e.g. cylindrical or spherical waves), the location of the localization of the particles within the wavefield is determined by the minima of the force potential U. In these cases, the pressure nodes and antinodes do not generally occur at the same spatial locations as the potential minima. But, similar to the plane wave case, the particles can generally be separated in a binary manner based upon their intrinsic properties relative to the background medium. The binary spatial positions where positive and negative acoustic contrast particles localize is now determined by minima in the force potential U.

Figure 1:
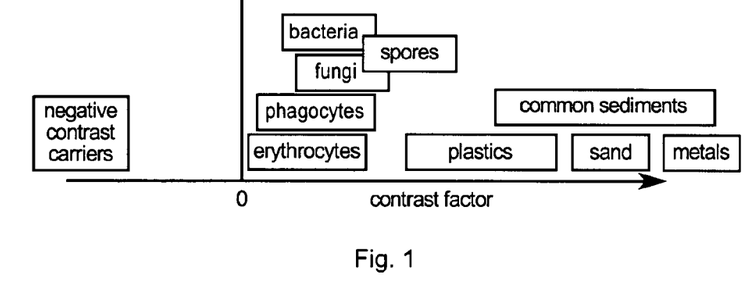
FIG. 1 is a schematic of contrast factors of various materials.

The contrast factors $f_1$ and $f_2$ demonstrate the significance of the relative values of the intrinsic properties of the particles and the medium. As shown in FIG. 1, for most particles in bio-research and biomedical applications including, but not limited to, erythrocytes, phagocytes, spores, yeast, fungi, and bacteria, as well as plastics, sand, common sediments, and metals, the contrast term is positive for particles in an aqueous background and all particles in a given sample are forced to the location of the same potential minima in the standing wave field. Therefore, acoustic binary separation of most biological particles in an aqueous solution is not feasible without adjusting the properties of the background medium. Separation of lipids from blood by using their negative acoustic contrast relative to the other blood components has been demonstrated by others.

The engineered acoustic contrast capture particles, when attached to bioparticles of interest, shifts the effective density and compressibility of the bioparticle/capture particle construct from positive to negative or negative to positive depending upon the preferred separation criteria relative to other particles in the system. As an example, an engineered capture particle is designed with low density and high compressibility relative to an aqueous medium. The particle is functionalized with anit-CD45 ligands and introduced into a blood sample to bind to CD45 markers on leukocytes. Under conditions where the blood sample is suspended in an aqueous buffer, both the erythrocytes and leukocytes have positive acoustic contrast and under the action of an acoustic standing wave, are forced to the same potential minima. By attaching an engineered particle with negative acoustic contrast to the leukocyte, the capture particle/leukocyte construct takes on negative acoustic contrast and be advantageously separated from the positive contrast population of erythrocytes.

Figure 2A:
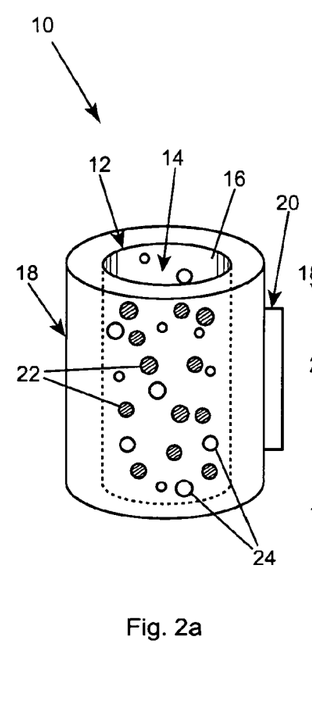
FIGS. 2a, 2b and 2c are schematic views of an apparatus in accordance with the present invention shown in various stages of acoustic field excitation.
Figures 2B, 2C:
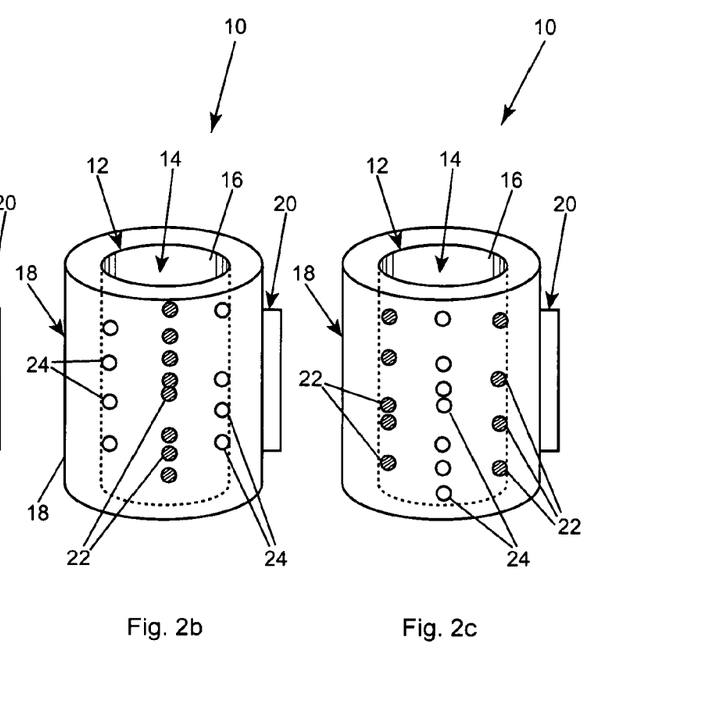

Referring now to FIGS. 2a-2c, apparatus in accordance with the present invention is indicated generally at 10. The apparatus 10 includes capillary 12 defining therein flow path or stream 14 in fluid communication with a medium source (not shown) within walls 16 of capillary 12. Capillary 12 is preferably constructed from quartz, glass, plastic, or any suitable material. Preferably, capillary 12 is circular in cross-section but those skilled in the art will appreciate that the cross-section of capillary 12 may be of any suitable geometry including, but not limited to, elliptical, square, rectangular or the like. The medium source may supply water, or any suitable liquid to flow path or stream 14, as will be appreciated by those skilled in the art. Capillary 12 is fully disposed within outer capillary 18. Vibration generator 20, such as a transducer the like, is disposed adjacent or mounted to an exterior surface of capillary 18 and is capable of producing at least one acoustic or displacement field within flow stream 14 of capillary 12. Alternatively, vibration generator 20 is a line-drive element, a displacement generator, or any other type of vibration generator adjacent or mounted to the exterior surface of capillary 12 capable of producing at least one acoustic or displacement field within flow path or stream 14 including, but not limited to, a contact aperture, a line contact, and a full encompassment of capillary 12, as will be appreciated by those skilled in the art. Under different symmetry excitations of the displacement field, the position of a force potential minima for positive contrast particles can be located along the central axis or flow stream 14 of capillary 12 or the force potential minima for positive contrast particles can be located at a position along wall 16. In these situations, the force potential minima for negative acoustic contrast particles will be located at the position not occupied by positive acoustic contrast particles (e.g. positive acoustic contrast particles along the central axis of flow stream 14 corresponds to negative acoustic contrast particles at a position along capillary wall 16 or negative acoustic contrast particles along the central axis of flow stream 14 corresponds to positive acoustic contrast particles at a position along capillary wall 16).

Disposed within flow stream 14 are bioparticles 22 and engineered acoustic contrast capture particles 24. As shown in FIG. 2a, with no acoustic field being generated by vibration generator 20 (i.e. the acoustic field is inactive), bioparticles 22 and negative contrast capture particles 24 are homogeneously distributed within flow stream 14 of capillary 12. As shown in FIG. 2b, when a dipole acoustic excitation and resulting dipole acoustic field is implemented by vibration generator 20, bioparticles 22 are focused to the center of flow stream 14 of capillary 12 (force potential minima for positive acoustic contrast particles) and engineered acoustic contrast capture particles with negative contrast 24 are transported to capillary wall 16 (force potential minima for negative acoustic contrast particles). Conversely, as shown in FIG. 2c, when an axisymmetric excitation and resulting axisymmetric acoustic field is implemented by vibration generator 20, all bioparticles 22 are sent to capillary wall 16 (force potential minima for positive acoustic contrast particles) and engineered acoustic contrast capture particles with negative contrast 24 are focused to the central axis of flow stream 14 of capillary 12 (force potential minima for negative acoustic contrast particles).

Figure 3A:
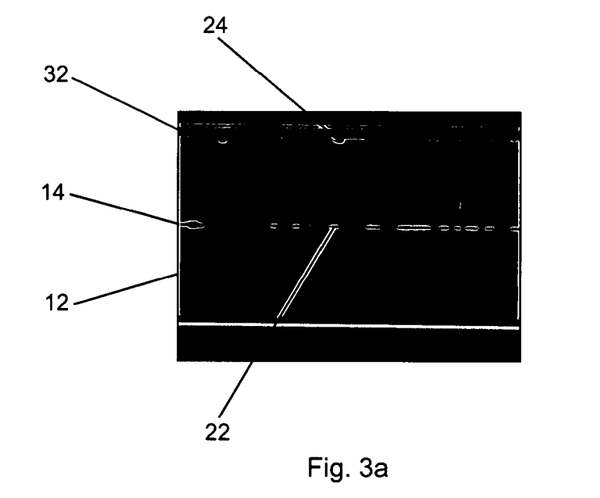
FIGS. 3a and 3b are microscopic photographs showing bioparticles and capture particles in a capillary of the present invention.
Figure 3B:
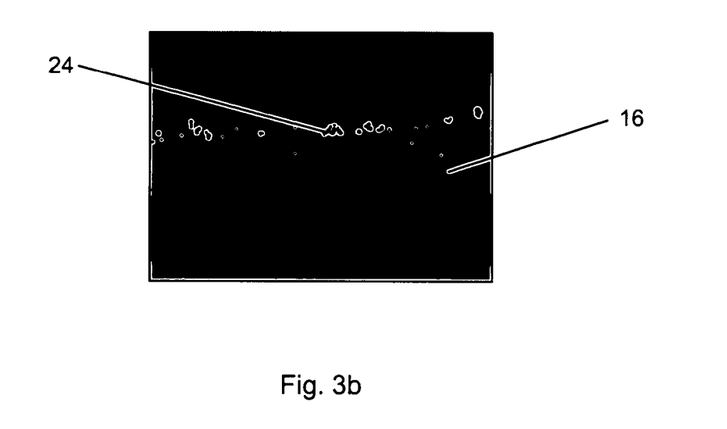

In a non-limiting example, background bioparticles 22 comprising 6.mu.m latex spheres and engineered acoustic contrast capture particles with negative contrast 24 comprising hollow, glass microspheres having low density, high compressibility characteristics were utilized in apparatus 10. Upon activation of vibration generator 20 generating a dipole acoustic field, such as shown in FIG. 2b, latex spheres 22 are focused to the center of flow stream 14 of capillary 12 while hollow glass spheres 24 are transported to wall 16 of capillary 12. This is shown in FIGS. 3a and 3b. A microscope with a narrow depth of field (not shown) is utilized to demonstrate the location of positive and negative contrast particles in apparatus 10. In FIG. 3a, the focal plane of the microscope intersects the central axis of flow stream 14 of capillary 12 where positive contrast particles 22 (latex spheres) have been focused along the axis and engineered negative contrast particles (glass microspheres) can be seen along capillary wall 16. In FIG. 3b, the focal plane of the microscope intersects an uppermost boundary of inner capillary wall 16. Here, negative contrast particles 24 (glass microspheres) are located adjacent capillary wall 16. Before activation of the acoustic field, particles 22 and 24 were homogenously distributed throughout capillary 12, such as shown in FIG. 2a.

Figure 4:
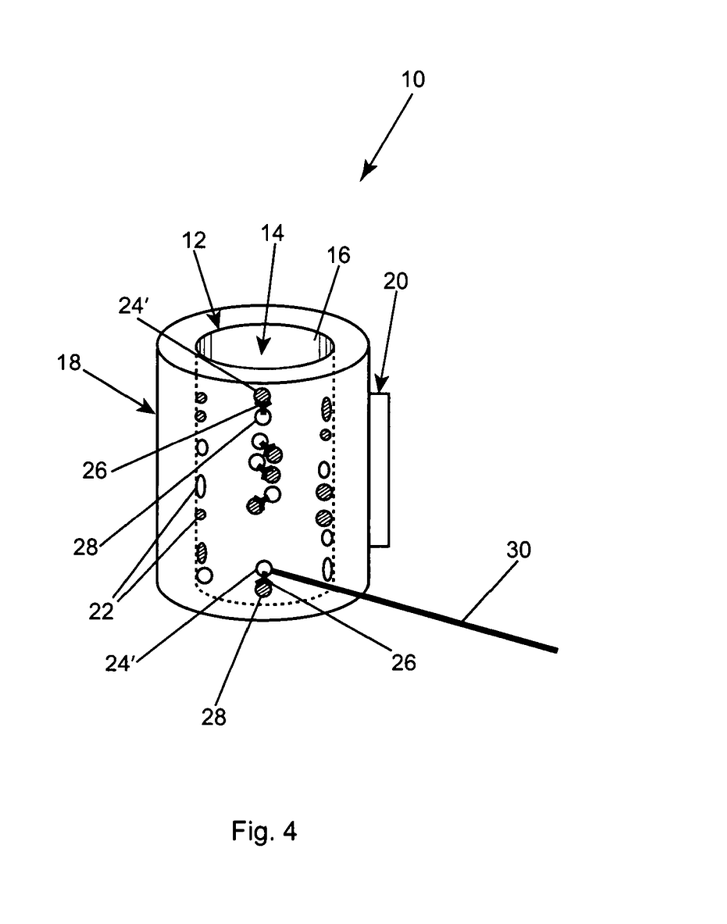
FIG. 4 is a schematic view of an apparatus in accordance with the present invention shown with an analyzing laser.

Referring now to FIG. 4, in this embodiment, engineered acoustic contrast capture particles with negative contrast 24' are functionalized with a specific coating to bind a target particle of interest, such as by functionalizing and coating engineered negative contrast capture particles 24' with antibody 26. Negative contrast capture particles 24' and antibodies 26 are mixed with a sample, incubated, and are bound to target cells 28. Target cells 28 are preferably biological molecules or particles. Upon flowing the sample through flow stream 14 of capillary 12 excited in an axisymmetric vibration mode by vibration generator 20, engineered negative contrast capture particles 24' with captured target cells 28 are focused to the center of flow stream 14 of capillary 12 for analysis by laser beam 30 (flow cytometry) or separation. The sample background particles (as they are bioparticles similar to bioparticles 22 shown in FIGS. 2a-2c) are forced to wall 16 of capillary 12. In a flow cytometer (not shown), laser beam 30 is focused to probe only those particles that transport along the axis of flow stream 14 of capillary 12.

Apparatus 10 preferably includes vibration generator 20 capable of driving capillary 12 in both axisymmetric and dipole modes, advantageously allowing for separate analysis of target particles 28 and remaining sample background particles 22. Engineered negative acoustic contrast capture particles 24 are transported to the position of a minima of the force potential for negative contrast particles in an acoustic field. Conversely, all other bioparticles 22 are transported to the position of a minima of the force potential for positive contrast particles in an acoustic field. In a flow cytometer, functionalized, engineered negative contrast capture particles 24' can be mixed with a sample. The untrapped sample or specific binding to capture particles 24' can be analyzed by placing or designing either the force potential minima for positive acoustic contrast particles or negative acoustic contrast particles at the center of the sample analysis flow stream 14.

Apparatus 10 advantageously takes advantage of the fact that most bioparticles, such as bioparticles 22 shown in FIG. 2a through FIG. 4, possess positive acoustic contrast and can be spatially isolated at a specific predetermined location defined by the force potential minima for positive acoustic contrast particles in an acoustic field, as the only particles that have negative contrast are acoustically similar to lipids/fats. By engineering capture particles 24 with a negative acoustic contrast, it is possible to separate engineered negative contrast capture particles 24 and 24' from biological particles 22 (and most other background particles 22) in a sample, as shown in FIG. 4. Under the action of an acoustic field, biological particles 22 will transport to the minima in the force potential for positive contrast particle, while engineered negative contrast capture particles 24 will transport to the minima in the force potential for negative contrast particles. In general, the spatial location defined by the force potential minima of positive and negative acoustic contrast particles are isolated from one another or at distinct predetermined locations within flow stream 14 of capillary 12.

Apparatus 10 advantageously employs engineered acoustic contrast capture particles with negative contrast 24 and 24' having a density/compressibility ratio less than that of the medium source (i.e. particles 24 and 24' are less dense and more compressible than the background fluid medium in the medium source, such as water). If the medium in flow stream 14 of capillary 12 is not water, the contrast properties of engineered acoustic contrast capture particles 24 and 24' may be advantageously adjusted according to the medium to take on either negative or positive contrast values. Engineered acoustic contrast capture particles 24 and 24' are used to capture bioparticles of interest 28 in a sample. When used in conjunction with an acoustically driven cylindrical channel, engineered acoustic contrast capture particles 24 and 24' can be forced to the center of flow stream 14 or wall 16 of capillary 12 and separated from the remaining sample constituents. This is very effective in new assays for flow cytometry that require target cells or constituents to be separated from a background. Alternatively, engineered acoustic contrast particles 24 and 24' have a positive acoustic contrast and have a density/compressibility ratio greater than that of the medium source (i.e. particles 24 and 24' are more dense and less compressible than the background fluid medium in the medium source, such as water).

Apparatus 10 may be advantageously utilized in commercial applications including, but not limited to, applications involving the separation of specific targets in biological samples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s), are hereby incorporated by reference.

What is claimed:

1. A system comprising:
   a capillary defining a flow path therein,
   a fluid medium source coupled to the capillary, the fluid medium source configured to supply a fluid medium to the capillary;
   a vibration generator coupled to the capillary; and
   a plurality of engineered negative acoustic contrast capture particles disposed in the fluid medium, each of the engineered negative acoustic contrast capture particles having a lower density/compressibility ratio than the density/compressibility ratio of the fluid medium.

2. The system of claim 1 wherein the vibration generator is configured to produce an acoustic field within the flow path of the capillary.

3. The system of claim 1 wherein the vibration generator is configured to produce a force potential minima in the fluid medium, the force potential minima driving the engineered negative acoustic contrast capture particles to the minima.

4. The system of claim 1 wherein the engineered negative acoustic contrast particles comprise a coating to bind a target particle in the fluid medium to the engineered negative acoustic contract particles.

5. The system of claim 1 further comprising a plurality of positive acoustic contrast particles, the positive acoustic contrast particles having a higher density/compressibility ratio than the density/compressibility ratio of the fluid medium.

6. The system of claim 5 wherein the vibration generator is configured to produce a first force potential minima in the flow path and a second force potential minima in the flow path, the first force potential minima configured to drive the engineered negative acoustic contrast particles to the first force potential minima, and the second force potential minima configured to drive the positive acoustic contrast particles to the second potential minima.

7. The system of claim 1 wherein the capillary is a cylindrical capillary.

8. The system of claim 5 wherein the positive acoustic contrast particles comprise bioparticles.

9. The system of claim 4 wherein the target particle has a negative acoustic contrast.

10. The system of claim 1 wherein the engineered negative acoustic contrast particles are glass microspheres.

11. A method of separating particles in a fluid medium, the method comprising:
    flowing the fluid medium in a capillary, the fluid medium comprising a plurality of engineered negative acoustic contrast particles and one or more targets; and
    imparting to the fluid medium, via a vibration generator coupled to the capillary, acoustic pressure,
    wherein the acoustic pressure is configured to generate a first force potential minima in the fluid media, the first force potential minima configured to drive the engineered negative acoustic contrast particles to the first force potential minima.

12. The method of claim 11 wherein the engineered negative acoustic contrast particles have a density/compressibility ratio that is less than the density/compressibility ratio of the fluid medium.

13. The method of claim 11 wherein the fluid medium comprises a plurality of positive acoustic contrast particles.

14. The method of claim 13 wherein the vibration generator is configured to generate a second force potential minima in the fluid media, the second force potential minima configured to drive the positive acoustic contrast particles to the second force potential minima.

15. The method of claim 13 wherein the positive acoustic contrast particles are bioparticles.

16. The method of claim 13 wherein the positive acoustic contrast particles have a density/compressibility ratio that is greater than the density/compressibility ratio of the fluid medium.

17. The method of claim 11 wherein the engineered negative acoustic contrast particles are glass microspheres.

18. The method of claim 11 wherein the engineered negative acoustic contrast particles comprise a coating to bind the one or more targets to the engineered negative acoustic contrast particle.

19. The method of claim 18 wherein the one or more targets have an acoustic contrast that has a lower density/compressibility ratio than the fluid medium.

20. The method of claim 18, wherein the one or more targets have a negative acoustic contrast.

* * * * *